US008859765B2

United States Patent
Wu et al.

(10) Patent No.: US 8,859,765 B2
(45) Date of Patent: Oct. 14, 2014

(54) PROCESS FOR THE MANUFACTURE OF CHIRAL CATALYSTS AND THEIR SALTS

(71) Applicant: Scinopharm Taiwan, Ltd., Shan-Hua (TW)

(72) Inventors: Ping-Yu Wu, Tainan (TW); Julian Paul Henschke, Summertown (AU)

(73) Assignee: ScinoPharm Taiwan, Ltd., Shan-Hua (TW)

( * ) Notice: Subject to any disclaimer, the term of this patent is extended or adjusted under 35 U.S.C. 154(b) by 23 days.

(21) Appl. No.: 13/689,703

(22) Filed: Nov. 29, 2012

(65) Prior Publication Data

US 2013/0150574 A1    Jun. 13, 2013

Related U.S. Application Data

(60) Provisional application No. 61/565,449, filed on Nov. 30, 2011.

(51) Int. Cl.
| | | |
|---|---|---|
| *C07D 265/30* | (2006.01) | |
| *C07C 311/02* | (2006.01) | |
| *C07D 295/096* | (2006.01) | |
| *C07C 303/36* | (2006.01) | |
| *C07D 413/12* | (2006.01) | |
| *C07B 53/00* | (2006.01) | |

(52) U.S. Cl.
CPC .......... *C07D 265/30* (2013.01); *C07D 295/096* (2013.01); *C07C 303/36* (2013.01); *C07D 413/12* (2013.01); *C07B 53/00* (2013.01)

USPC .............................. 544/106; 544/111; 564/80

(58) Field of Classification Search
None
See application file for complete search history.

(56) References Cited

U.S. PATENT DOCUMENTS 8,168,835 B2    5/2012   Uang et al.
2011/0269955 A1  11/2011   Uang et al.

OTHER PUBLICATIONS

Wu et al., "Asymmetric synthesis of propargylic alcohols catalyzed by (−)-MITH," Tetrahedron: Asymmetry, 2009, vol. 20, pp. 1837-1841.
Wu et al., Asymmetric addition of dimethylzinc to alpha-ketoesters catalyzed by (−)-MITH, Journal of Organic Chemistry, 2008, vol. 73, pp. 6445-6447.
Wu et al., "Highly enantioselective synthesis of E-allylic alcohols," Journal of Organic Chemistry, 2007, vol. 72, pp. 5935-5937.
Wu et al., "Asymmetric synthesis of functionalized diarylmethanols catalyzed by a new gamma-amino thiol," Journal of Organic Chemistry, 2006, vol. 71, pp. 833-835.
Osorio-Planes et al., Org. Lett., 2012, 14, 1816-1819.
International Search Report and Written Opinion, PCT application No. PCT/IB2012/002910, mailed Jun. 14, 2013, 8 pages.

*Primary Examiner* — Nyeemah A Grazier
(74) *Attorney, Agent, or Firm* — Kilpatrick Townsend & Stockton LLP; William B. Kezer

(57) ABSTRACT

The present invention provides efficient and economical methods for synthesis of (−)-2-exo-morpholinoisoborne-10-thiol, its enantiomer, and related chiral catalysts. Novel compounds and methods of asymmetric synthesis are also disclosed.

11 Claims, 5 Drawing Sheets

PROCESS FOR THE MANUFACTURE OF CHIRAL CATALYSTS AND THEIR SALTS

CROSS-REFERENCES TO RELATED APPLICATIONS

This application claims the benefit of priority to U.S. Provisional Application Ser. No. 61/565,449, filed Nov. 30, 2011, the entire content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION ((−)-2-exo-morpholinoisoborne-10-thiol, abbreviated as "(−)-MITH" and classified as a γ-aminothiol ligand, is an efficient catalyst that induces the stereoselective formation of chiral carbon centers in certain reactions (*J. Org. Chem.* 2006, 71, 833-835). (−)-MITH (CAS No. 874896-16-9) has the systematic name ((1R,2R,4R)-7,7-dimethyl-2-morpholino-bicyclo[2.2.1]heptan-1-yl)methanethiol and the structure:

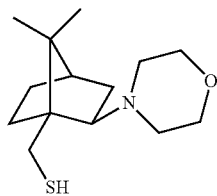

(Ia)

The abbreviation MITH is used herein to apply to (−)-MITH and its enantiomer (+)-MITH ((+)-2-exo-morpholinoisoborne-10-thiol). It is particularly useful as a chiral catalyst in organozinc addition reactions to α-ketoesters and aldehydes, including methylation, ethylation, vinylation, propargylation, and arylation (see *J. Org. Chem.* 2006, 71, 833-835; *Chem. Asian J.* 2012, 7, 2921-2924; *J. Org. Chem.* 2007, 72, 5935-5937; *Tetrahedron: Asymmetry* 2009, 20, 1837-1841; *J. Org. Chem.* 2008, 73, 6445-6447; U.S. Pat. No. 8,168,835; U.S. Pat. Appl. 2011/0269955).

MITH has demonstrated utility for inducing high stereoselectivity in asymmetric carbon-carbon bond-forming reactions. However, its physical properties (i.e., non-solid oily form and instability under ambient conditions) and the reported method for its synthesis significantly limit its manufacture on large enough scales to be useful in the pharmaceutical industry. The synthesis of MITH that is disclosed in the peer-reviewed literature involves six formal reaction steps and various work-up and purification steps to access the product from the commercially available starting material, camphorsulfonic acid (see FIG. 1 and *J. Org. Chem.* 2006, 71, 833-835). Although the synthetic route itself is efficient, giving a 25% overall yield, the synthetic route is not suitable for scale-up for manufacture. Scale-up is unsuitable for a number of reasons, including those specified above.

For instance, triphenylphosphine is required to reduce a sulfonyl chloride intermediate to the desired thiol (A-2 in FIG. 1). The removal of the phosphine oxide byproduct of this reaction was problematic and multiple recrystallizations of A-2 followed by column chromatographic purification were required.

Scale-up is further complicated by the need for protection and deprotection steps. Owing to the high reactivity of the thiol intermediate A-2, the thiol functional group was protected as a benzyl thioether (A-3 in FIG. 1). Benzyl thioethers are difficult to deprotect to recover the thiol compound, and harsh reaction conditions were required in the final deprotection step. The use of a Birch reduction reaction in the deprotection step requires the handling of sodium metal and its dissolution in liquid ammonia. Sodium is flammable upon contact with moisture, water, acids and protic solvents such as alcohols, making scale-up potentially hazardous. Furthermore, ammonia boils at −33° C., and very low temperatures (−78° C.) are required to prevent dangerous pressure build-up. The use of such conditions should be avoided on manufacturing scales for safety concerns.

In addition, the need for multiple column purification operations limits suitability for scale-up. The known synthetic route requires the use of six chromatographic purifications steps (see *J. Org. Chem.* 2006, 71, 833-835). The product itself is also an oil and is purified by column chromatography. For manufacturing, purification of organic compounds using column chromatography typically results in higher production costs due to the increases in required time and materials as compared to other purification methods. Large volumes of organic solvents must be recycled or disposed, which has environmental and monetary costs. A chromatography-free process for the synthesis of MITH and MITH analogs would therefore be highly advantageous, expanding the utility of MITH as a catalytic or stoichiometric reagent in the pharmaceutical and chemical industries.

U.S. Pat. Appl. 2011/0269955 disclosed a synthetic route including the use of a morpholino sulfonamide functional group as a masked thiol in place of the previously used benzyl protecting group. This allowed for a direct, one-step conversion of the final intermediate B-6 to the thiol (i.e., MITH) using LiAlH$_4$ as a reducing agent (FIG. 2). Although the synthesis provided improved scalability by removing the dangerous deprotection step in the original method, the overall yield was lower (20%). Furthermore, the method disclosed in U.S. Pat. Appl. 2011/0269955 is still problematic from an industrial perspective due to: i) the UV-transparency of all synthetic intermediates bearing morpholinosulfonamide substituents, which prevents reaction monitoring by ordinary UV-HPLC. Reaction monitoring is very important during manufacturing as it allows in-process control which ensures effective control of reaction leading to reproducible yields and product quality; ii) the need for purification of several intermediates by column chromatography; and iii) the large quantity of lithium aluminum hydride used in the final reduction step, the handling of which is particularly dangerous on manufacturing scales due to its extremely pyrophoric nature.

Moreover, organic compounds such as MITH that are oils rather than solids present certain disadvantages during manufacturing, including: i) they are often less stable than solids and can therefore require less convenient long-term storage conditions, such as in an inert atmosphere and/or at low temperatures, and ii) they are more difficult to transfer from one vessel to another vessel, such as is required for charging reagents into reactors. MITH is only stable for a period of days to weeks under ambient conditions. A solid, preferably crystalline, form of MITH or a MITH analog would be highly advantageous since it would be more stable, easier to transport and store, and easier to handle in industrial-scale chemical transformations.

Given the foregoing, it is clear that there is an unmet need for a convenient, safe, and scalable manufacturing process for MITH and related compounds. The present invention addresses this and other needs.

BRIEF SUMMARY OF THE INVENTION

In one aspect, the present invention provides a process for preparing a compound of formula (I)

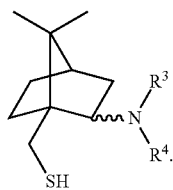
(I)

The process includes:
i) contacting a sulfonamide of formula (II)

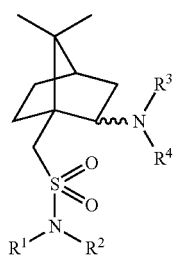
(II)

with a first reducing agent under conditions sufficient to provide a disulfide compound of formula (III)

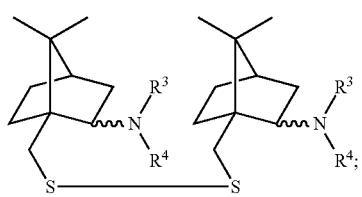
(III)

and
ii) contacting the disulfide compound of formula (III) with a second reducing agent under conditions suitable to form a compound of formula (I); wherein
$R^1$ and $R^2$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl;
$R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl; or optionally
$R^3$, $R^4$ and N can together form a $C_{3-10}$ heterocycle.

In a second aspect, the present invention provides a process for preparing a compound of formula (I). The process includes:

i) converting a compound of formula (V)

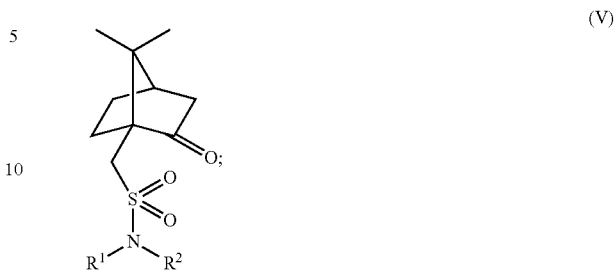
(V)

to a compound of formula (VII)

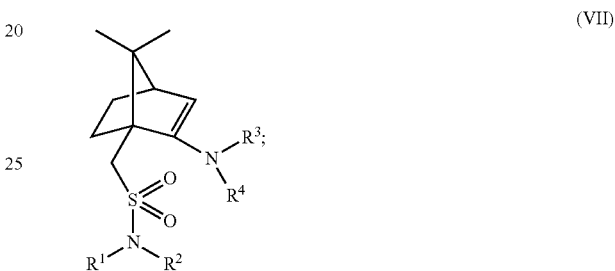
(VII)

and
ii) converting the compound of formula (VII) to the compound of formula (I), wherein $R^1$, $R^2$, $R^3$, and $R^4$ are defined as above.

In a third aspect, the present invention provides novel compounds including:

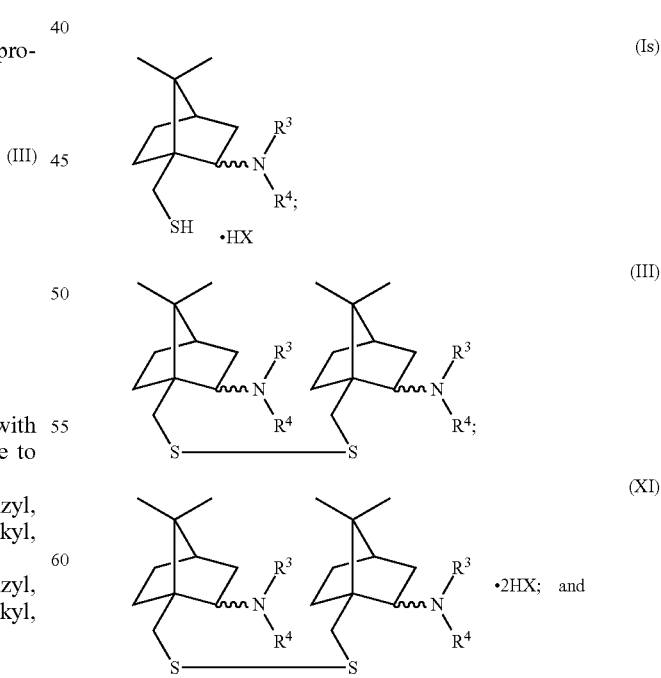

-continued

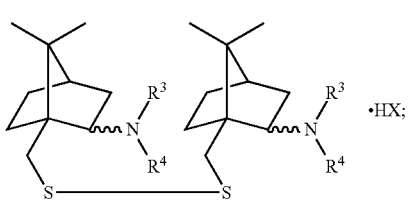

(XI')

wherein R³ and R⁴ are defined as above, and HX is a Brønsted acid where H is a proton and X is a conjugate base.

In a fourth aspect, the present invention provides a method of asymmetric synthesis including contacting a compound of formula (Is), (III), or (XI) with reactants in an asymmetric transformation to stereoselectively provide a product.

DETAILED DESCRIPTION OF THE INVENTION

Figure 1:
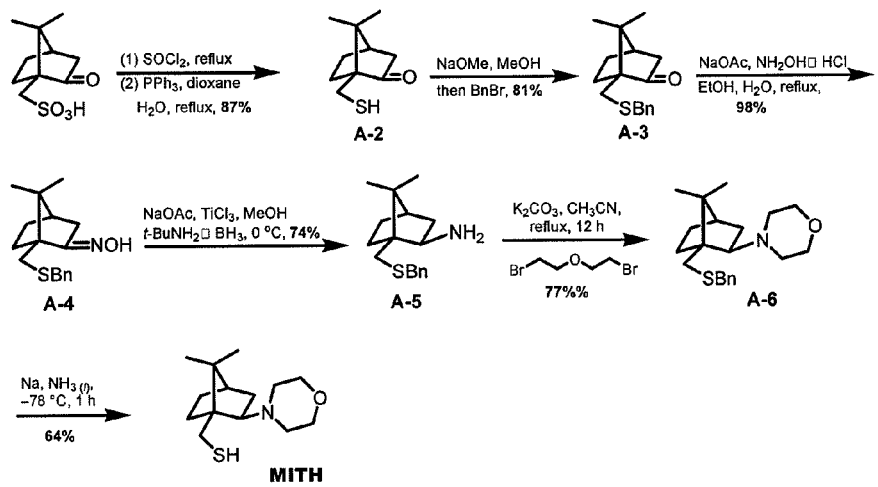
FIG. 1 shows the schematic for MITH synthesis as disclosed in *J. Org. Chem.* 2006, 71, 833-835.
Figure 2:
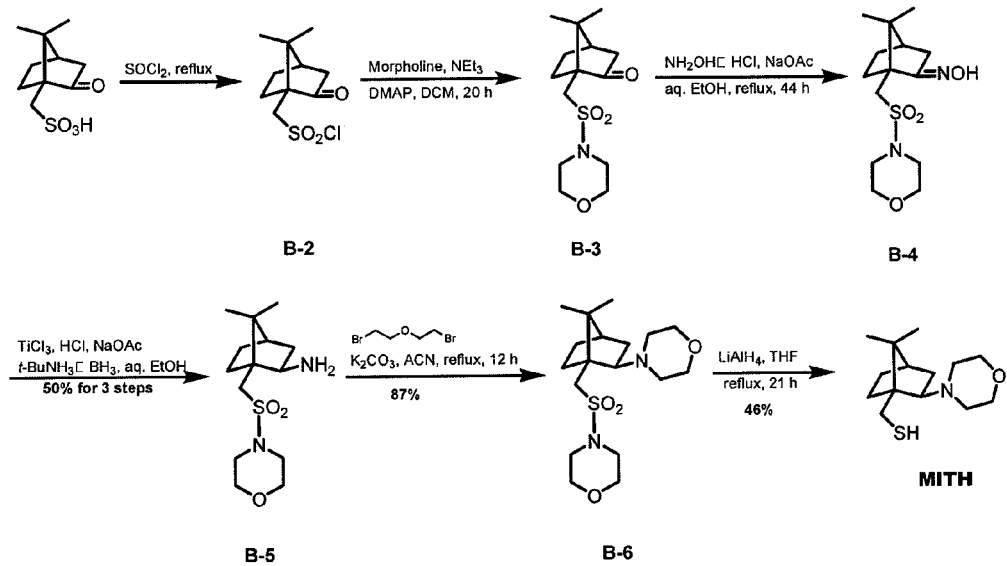
FIG. 2 shows the schematic for MITH synthesis as disclosed in U.S. Pat. Appl. 2011/0269955.

The present invention provides methods for the synthesis of optically active catalysts for use in asymmetric synthesis. These catalysts act as ligand of metals. The invention is based on the surprising discovery that compounds of formula (I) can be accessed via intermediate compounds (II) and (III) using mild conditions. Key products and intermediates in the inventive methods can be isolated and purified without the need for expensive chromatographic steps. In particular, benzyl sulfonamides, disulfides, and the catalyst salts were unexpectedly found to have solubility properties that allow for efficient isolation and purification. Furthermore, a novel method for sulfonamide reduction was unexpectedly found to provide thiol-containing catalysts with better yield and quality than alternative routes. Accordingly, the inventive methods allow for scale-up of the catalysts for industrial applications. The present invention also provides novel compounds and methods for asymmetric synthesis as disclosed herein.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents which can be produced in the reaction mixture.

As used herein, the term "reducing agent" refers to an agent capable of reducing another compound. The reducing agent can be a metal, an organic compound, an inorganic compound, a complex of a metal and an inorganic compound or a complex of a metal and an organic compound. Examples of reducing agents include, but are not limited to, alkali metals, metal hydrides, thiol- and phosphine-based reducing agents, ascorbic acid, and the like.

The term "alkyl," by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e., $C_1$-$C_8$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene, and adamantane. For example, $C_{3-8}$ cycloalkyl includes cyclopropyl, cyclobutyl, cyclopentyl, cyclohexyl, cyclooctyl, and norbornane.

As used herein, the term "heterocycloalkyl" and "heterocycle" refer to a ring system having from 3 ring members to about 20 ring members and from 1 to about 5 heteroatoms such as N, O and S as ring vertices. Additional heteroatoms can also be useful, including, but not limited to, B, Al, Si and P. The heteroatoms can also be oxidized, such as, but not limited to, —S(O)— and —S(O)$_2$—. Heterocycloalkyl includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl. For example, the term $C_{4-9}$ heterocycloalkyl refers to a 4- to 9-membered ring (including bicyclic and polycyclic rings) having the indicated number (4-9) of ring vertices with at least one heteroatom ring member.

As used herein, the terms "aryl" and "aromatic ring," by themselves or as part of another substituent, refer to a polyunsaturated, hydrocarbon group which can be a single ring or multiple rings (up to three rings) which are fused together or linked covalently. Non-limiting examples of aryl groups include phenyl, naphthyl and biphenyl.

As used herein, the term "arylalkyl" refers to a radical having an alkyl component and an aryl component, where the alkyl component links the aryl component to the point of attachment. The alkyl component is as defined above, except that the alkyl component is at least divalent in order to link to the aryl component to the remainder of the molecule. The aryl component is as defined above. Examples of arylalkyl groups include, but are not limited to, benzyl and phenylethyl.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. Heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, and thienyl. For example, the term $C_{5-9}$ heteroaryl refers to a 5- to 9-membered ring (including bicyclic rings) having the indicated number (5-9) of ring vertices with at least one heteroatom ring member.

As used herein, the term "alkenyl" refers to either a straight chain or branched hydrocarbon having at least one double bond. Unless otherwise specified, the alkenyl groups of the present invention contain 2 to 8 carbon atoms. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkynyl" refers to either a straight chain or branched hydrocarbon having at least one triple bond. Unless otherwise specified, the alkynyl groups of the present invention contain 2 to 8 carbon atoms. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

The terms "sulfide", "thiol," and "mercapto" refer to a radical having the structure —S—H, where sulfur is the point of attachment to an organic molecule. A sulfide can be oxidized to a disulfide containing a S—S bond, although one of skill in the art will appreciate that disulfides can be obtained via other routes in addition to sulfide oxidation. A disulfide can be a mixed disulfide, having a structure R—S—S—R', wherein R and R' may be independently hydrogen, alkyl, aryl, aralkyl, cycloalkyl, heterocyloalkyl, or heteroaryl as defined above. Certain highly reactive thiols can be used as reducing agents sufficient for reducing a disulfide; examples of such thiols include dithiothreitol, β-mercaptoethanol, and the like.

The term "sulfonamide" refers to the radical having the structure —$SO_2NR'R''$ where sulfur is the point of attachment to an organic molecule and R' and R'' may be independently hydrogen, alkyl, aryl, aralkyl, cycloalkyl, heterocyloalkyl, or heteroaryl as defined above. N, R', and R'' together may also form heterocyloalkyl or heteroaryl as defined above.

As used herein, the term "polymer support" refers to a polymeric material which can be derivatized to include a compound of the present invention. Examples of suitable polymer supports include, but are not limited to, polystyrene, polyurethane, polystyrene-divinylbenzene copolymer, and derivatives thereof. Except for the reactive sites intended for derivitization, polymer support materials are generally resistant to the variety of chemical reaction conditions to which they may be subjected. One of skill in the art will appreciate that other polymer supports are useful in the present invention.

As used herein, the term "leaving group" refers to a functional group that is displaced by a nucleophile such as an amine, a thiol, or an alcohol. In some embodiments, the leaving group is displaced by an amine to provide a sulfonamide moiety. Examples of leaving groups include, but are not limited to, halides (including chloride and fluoride), activated alcohols (as displaced from sulfonyl esters), sulfonic acids (as displaced from sulfonic anhydrides), and sulfinic acids (as displaced from α-disulfones).

As used herein, the term "salt" refers to acid or base salts of the compounds used in the methods of the present invention. The term "acid salt," in particular, refers to the ionic compound resulting from reaction of a basic organic compound with a suitable acid. Examples of suitable acids include, but are not limited to, inorganic/mineral acids (hydrochloric acid, hydrobromic acid, phosphoric acid, and the like), carboxylic acids (acetic acid, propionic acid, glutamic acid, citric acid, and the like) salts, and organic sulfonic acids (p-toluenesulfonic acid, trifluoromethanesulfonic acid, and the like).

As used herein, the term "asymmetric synthesis" refers to a chemical reaction or sequence of chemical reactions in which one or more new elements of chirality are formed in a substrate molecule and which produces enantiomeric or diastereoisomeric products in unequal amounts. The resulting product distribution can be expressed as stereomeric excess, which is the absolute difference between the mole fraction of each stereoisomer in a pair of enantiomers or diastereomers (i.e., enantiomeric excess or diastereomeric excess, respectively). The terms "stereoselective" and "stereoselectively" refer to chemical processes that provide a product, the majority of which consists of a single enantiomer or diastereomer (see, IUPAC. *Compendium of Chemical Terminology*, 2nd ed. Blackwell Scientific Publications, Oxford, 1997).

As used herein, the term "ligand" refers to an organic molecule capable of binding to a functional group, typically a metal atom, to provide a catalyst for use in a chemical transformation. The ligands of the present invention can be used as "chiral ligands" for asymmetric synthesis. Chiral ligands typically consist of single stereoisomer, and the structure of the ligand induces formation of a particular enantiomeric or diastereomeric product.

Figure 3:
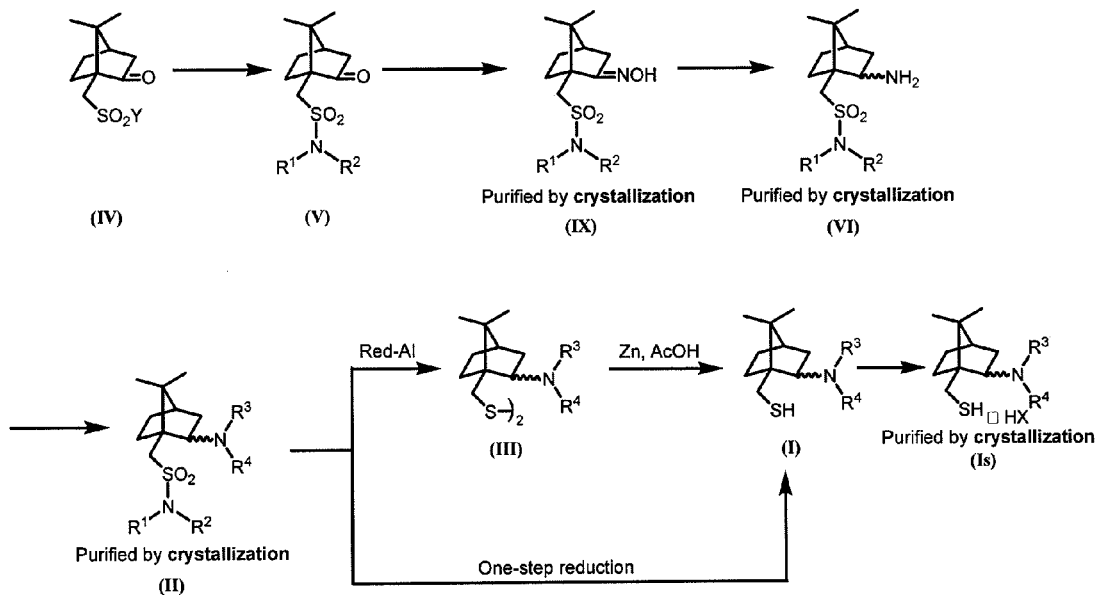
FIG. 3 shows the schematic for synthesis of MITH, MITH•HCl, and analogs according to the methods of the present invention.

In contrast to methods utilizing other thiol protecting groups in MITH precursors, the methods of the present invention utilize a protected sulfonamide (FIG. 3). This obviates the need for dangerous, non-scalable deprotection steps involving sodium in liquid ammonia. Rather, the sulfonamides in the present methods can be converted to the requisite thiol functional group by reduction in one reaction step (i.e., from sulfonamide (II) to thiol (I) in FIG. 3), or in two-reaction steps (i.e., from sulfonamide (II) to disulfide (III), then to thiol (I)). In particular, the two-step reduction process results in improved yields and product quality.

Furthermore, the present invention eliminates the need for the chromatographic purification steps that are required in the methods discussed above. In particular, the benzyl sulfonamides and related compounds employed in the present methods exhibit good crystallinity, allowing for purification of certain intermediates via crystallization. The target compounds can also be purified without the need for column chromatography by conversion to a crystalline salt derivative (Is). Eliminating the need for column chromatography is very advantageous because it reduces costs in terms of materials and operation time.

In one aspect, the present invention provides a process for preparing a compound of formula (I)

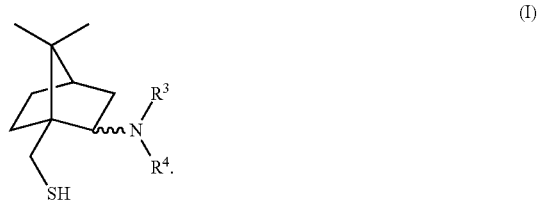

(I)

The process includes:
i) contacting a sulfonamide of formula (II)

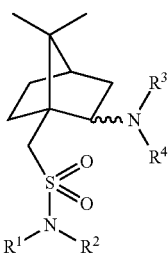

(II)

with a first reducing agent under conditions sufficient to provide a disulfide compound of formula (III)

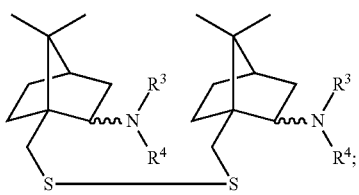

(III)

and
ii) contacting said disulfide compound of formula (III) with a second reducing agent under conditions suitable to form a compound of formula (I); wherein
$R^1$ and $R^2$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl;
$R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl; or optionally
$R^3$, $R^4$, and N can together form a $C_{3-10}$ heterocycle.

The first reducing agent employed in the methods of the present invention can be any suitable reducing agent. In some embodiments, the first reducing agent is an aluminum hydride reagent. Examples of aluminum hydride reagents include, but are not limited to, sodium bis(2-methoxyethoxy)aluminum hydride (Red-Al® or Vitride®), and lithium aluminum hydride (LiAlH$_4$), diisobutylaluminium hydride. In particular, sodium bis(2-methoxyethoxy)aluminum hydride is preferred when used on a manufacturing scale as it is non-pyrophoric and less moisture sensitive and can be used in aromatic organic solvents such as toluene. Accordingly, in some embodiments, the first reducing agent is sodium bis(2-methoxyethoxy)aluminum hydride.

The second reducing agent employed in the methods of present invention can be any suitable reducing agent. In general, the second reducing agent is a reagent that is capable of reducing a disulfide to a thiol. In some embodiments, the second reducing agent is a metal including zerovalent metals, zerovalent metal alloys, and non-zerovalent metals, a metal hydride, or a highly reactive thiol. Examples of metal hydrides include, but are not limited to, sodium bis(2-methoxyethoxy)aluminum hydride (Red-Al®), lithium aluminum hydride (LiAlH$_4$), diisobutylaluminium hydride (i-Bu$_2$AlH), sodium cyanoborohydride (NaBH$_3$CN), and sodium borohydride (NaBH$_4$). Examples of zerovalent metal reducing agents include, but are not limited to, zinc metal, sodium metal, potassium metal, aluminum metal, iron metal and magnesium metal. Examples of non-zerovalent metal reducing agents include, but are not limited to titanium (III) compounds, iron (II) compounds, copper (I) compounds, and samarium (II) compounds. Examples of highly reactive thiols include, but are not limited to, dithiothreitol, ethyl mercaptan, glutathione, ethane dithiol, dithiobutylamine, and 3-mercapto-1,2-propanediol. Zinc metal is non-pyrophoric and is suitable for use as a reagent on manufacturing scales. In some embodiments, the reducing agent is zinc metal.

As shown in FIG. 3, sulfonamide compounds (II) may be reduced to provide thiols (I) in one step or two steps. In certain instances, the overall yield and quality of the thiol product is better for the two-step reduction process. For example, the reduction of sulfonamide (IIa) using hydride reagents such as sodium bis(2-methoxyethoxy)aluminum hydride was unexpectedly found to provide disulfide (IIIa) as the major product rather than thiol (Ia). However, the two-step reduction of sulfonamide (IIa) using sodium bis(2-methoxyethoxy)aluminum hydride in the first step and zinc metal with acetic acid in the second step provided MITH (Ia) with an improved overall yield (70%). In addition to this surprising improvement in efficiency, the two-step reduction method provided other advantages. Unlike MITH, disulfide (IIIa) is a solid, for example, and can be readily purified via recrystallization. Moreover, disulfide (IIIa) can itself be used for catalysis of asymmetric reactions.

In contrast, the one-step reduction of sulfonamide (IIa) to MITH (Ia) using metal hydrides generally occurred more slowly in lower yield. Without wishing to be bound by any particular theory, one-step reduction of certain sulfonamides with metal hydrides is believed to be slowed by the formation of disulfides which react slowly under those reduction conditions. Therefore, it can be more efficient to reduce a sulfonamide compound to the corresponding disulfide compound in a first step, and then reduce the disulfide compound to the thiol compound using more suitable conditions in a second step. This unprecedented discovery led to the development of the inventive methods for the conversion of sulfonamides to the desired catalysts. One of skill in the art will appreciate, however, that a one-step reduction or a two-step reduction may be suitable depending on the particular sulfonamide employed in the methods of the invention.

As described above, $R^1$ and $R^2$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl. In some embodiments, at least one of $R^1$ and $R^2$ is a benzyl group or a substituted benzyl group. Benzyl groups may be substituted with one more substituents independently selected from the group consisting of halogen, alkyl, trifluoromethyl, hydroxy, alkoxy, trifluoromethoxy, amino, monoalkylamino, or dialkylamino. In some embodiments, at least one of $R^1$ and $R^2$ is hydrogen. The use of a benzyl sulfonamide functional group in compounds of formula (II), in particular, imparts good crystallinity to the compounds and allows for purification of key intermediates via crystallization, eliminating the need for chromatographic purification. Compound purification via recrystallization is advantageous, particularly on manufacturing scales, because it is less wasteful in terms of materials, time, and cost than purification via chromatography.

As described above, $R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl. Optionally $R^3$, $R^4$, and N can together form a $C_{3-10}$ heterocycle. In some embodiments, $R^3$, $R^4$, and N together form a morpholine group.

Figure 5:
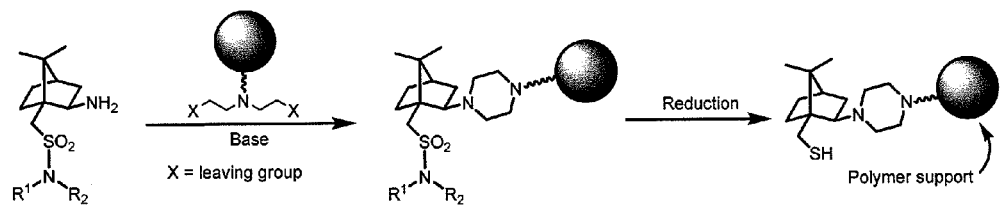
FIG. 5 shows a polymer-supported MITH analog.

In related embodiments, $R^3$, $R^4$, and N together form part of a polymer support or link to a polymer support. Polymer-supported catalysts play an important role in fine chemical and pharmaceutical intermediate synthesis. Polymer-supported catalysts can act as ordinary catalysts, but after their use they can be easily removed from the reaction by simple filtration and can therefore be conveniently recycled and reused. An advantage of the use of the polymer-supported catalysts is that they can be used at higher catalyst loadings without concern for the cost of the catalyst since they can be conveniently recycled (for an example of polymer-supported catalysts in organozinc reactions, see *Org. Lett.* 2012, 14, 1816-1819). For organozinc reactions, in particular, high enantioselectivity is often associated with high catalyst loading. Therefore, a polymer-supported MITH analog provides for efficient and highly enantioselective transformations. A polymer supported analog of MITH can be prepared as outlined in FIG. 5. By changing the alkylating dibromide used for solution synthesis to a polymer-bound bis(bromoethyl) amine, polymer-supported MITH is provided using the same synthetic strategy for the solution synthesis. This is also applicable for the synthesis of the enantiomeric polymer-supported MITH analog.

In some embodiments, the compound of formula (II) is the exo-diastereomer $II_x$:

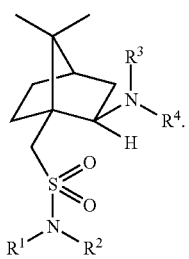

(II$_x$)

In some embodiments of the present invention, the process for the preparation of a compound of formula (I) further includes:

iii) converting the compound of formula (I) to its acid salt (Is)

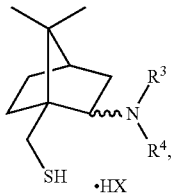

(Is)

by contacting the compound of formula (I) with an acid (HX); wherein

HX is selected from an inorganic/mineral acid, a carboxylic acid, and an organic sulfonic acid.

In some embodiments, the compound of formula (Is) is the exo-diastereomer:

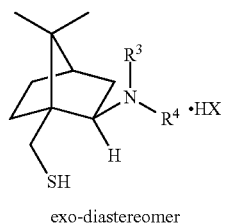

(Is)

exo-diastereomer

The acid HX can be any suitable acid. Suitable acids include inorganic/mineral acids such as hydrochloric acid, hydrobromic acid, hydroiodic acid, phosphoric acid and sulfuric acid, carboxylic acids such as trifluoroacetic acid, and organic sulfonic acids such as methanesulfonic acid, trifluoromethanesulfonic acid, and p-toluenesulfonic acid. In some embodiments, the acid HX is HCl (hydrochloric acid).

In some embodiments, the compound of formula (I) is selected from compound (Ia) and the enantiomer of compound (Ia)

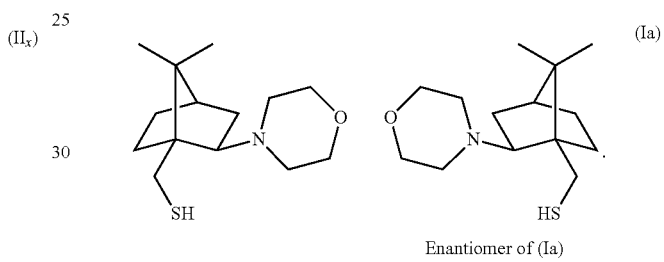

Enantiomer of (Ia)

In some embodiments, the sulfonamide of formula (II) is selected from compound (IIa) and the enantiomer of compound (IIa)

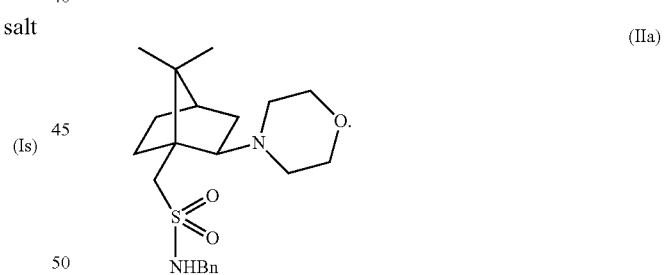

(IIa)

In some embodiments, the compound of formula (III) is selected from compound (IIIa) and the enantiomer of compound (IIIa)

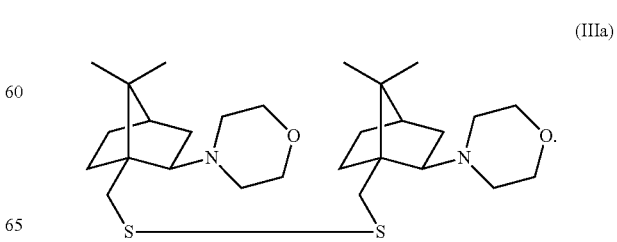

(IIIa)

In some embodiments, the compound of formula (Is) is selected from compound (Ib) and the enantiomer of compound (Ib)

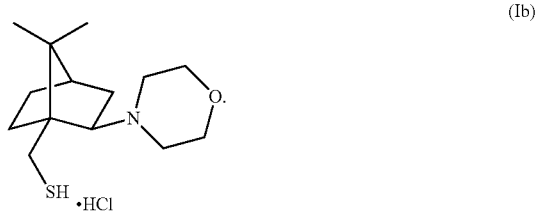 [SMILES: CC1(C)C2CCC1(CS)C(N1CCOCC1)C2 ; Cl]

(Ib)

One of skill in the art will appreciate that if any of the compounds of formula (I), (Is), (II), or (III) is present as a given enantiomer, then the other compounds, if present, will have the same stereochemical configuration.

Figure 6:
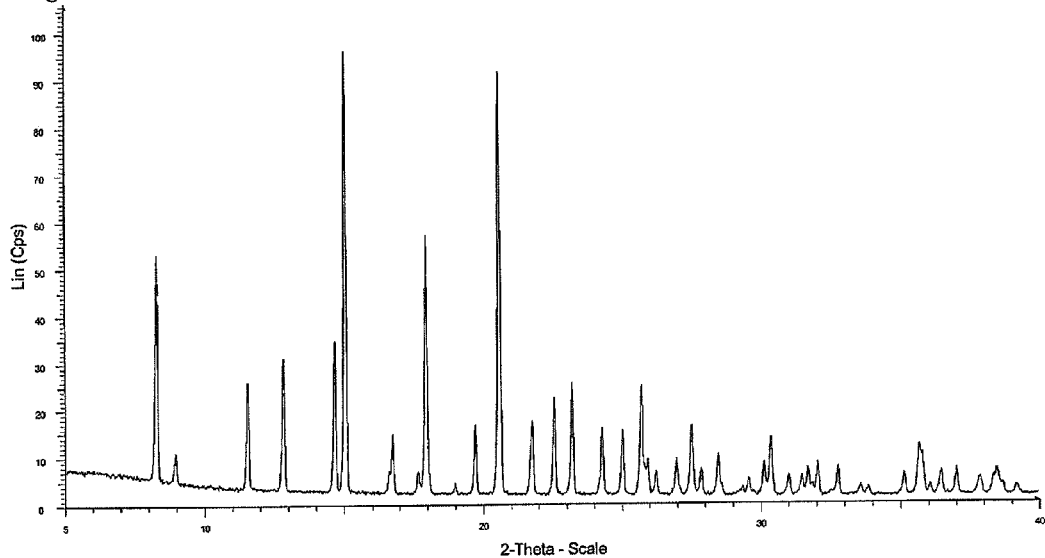
FIG. 6 shows the X-ray powder diffraction pattern of a crystalline form of MITH•HCl.

In contrast to MITH, the acid salt (Ib) is crystalline and is stable under ambient conditions. Particularly useful acids for salt formation have non-coordinating, non-nucleophilic conjugate bases and do not interfere with catalysis of asymmetric transformations. In some embodiments, MITH (Ia) is contacted with hydrochloric acid to produce the HCl salt (Ib). Salt (Ib) is a non-hygroscopic, white powder that can be readily purified by crystallization. The XRPD pattern of MITH salt (Ib) shows that it is crystalline (FIG. 6).

An inherent lack of stability frequently complicates the synthesis and application of typical aminothiol compounds for use as ligands. This instability results from the fact that free thiols can readily be oxidized to the corresponding disulfides in the presence of oxygen (see Scheme 1). This can occur upon exposure to the air.

Scheme 1. The oxidation of thiols to disulfides

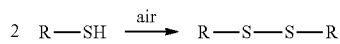

Figure 7:
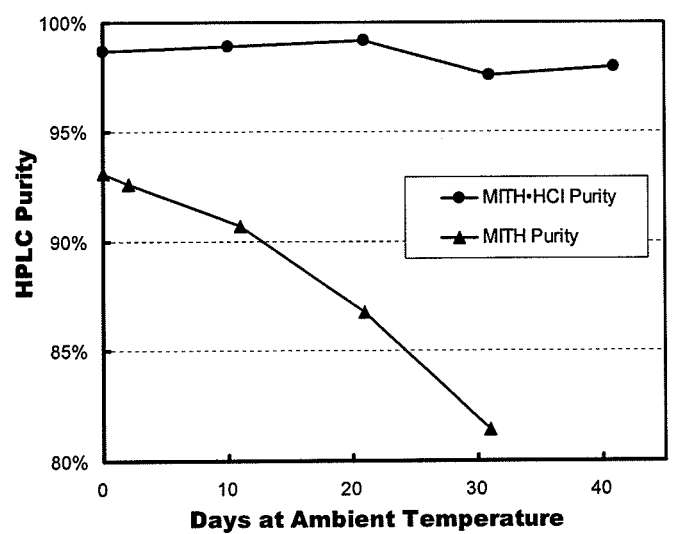
FIG. 7 shows the stability of MITH and MITH•HCl during storage at ambient temperature, as assessed by HPLC.
Figure 8:
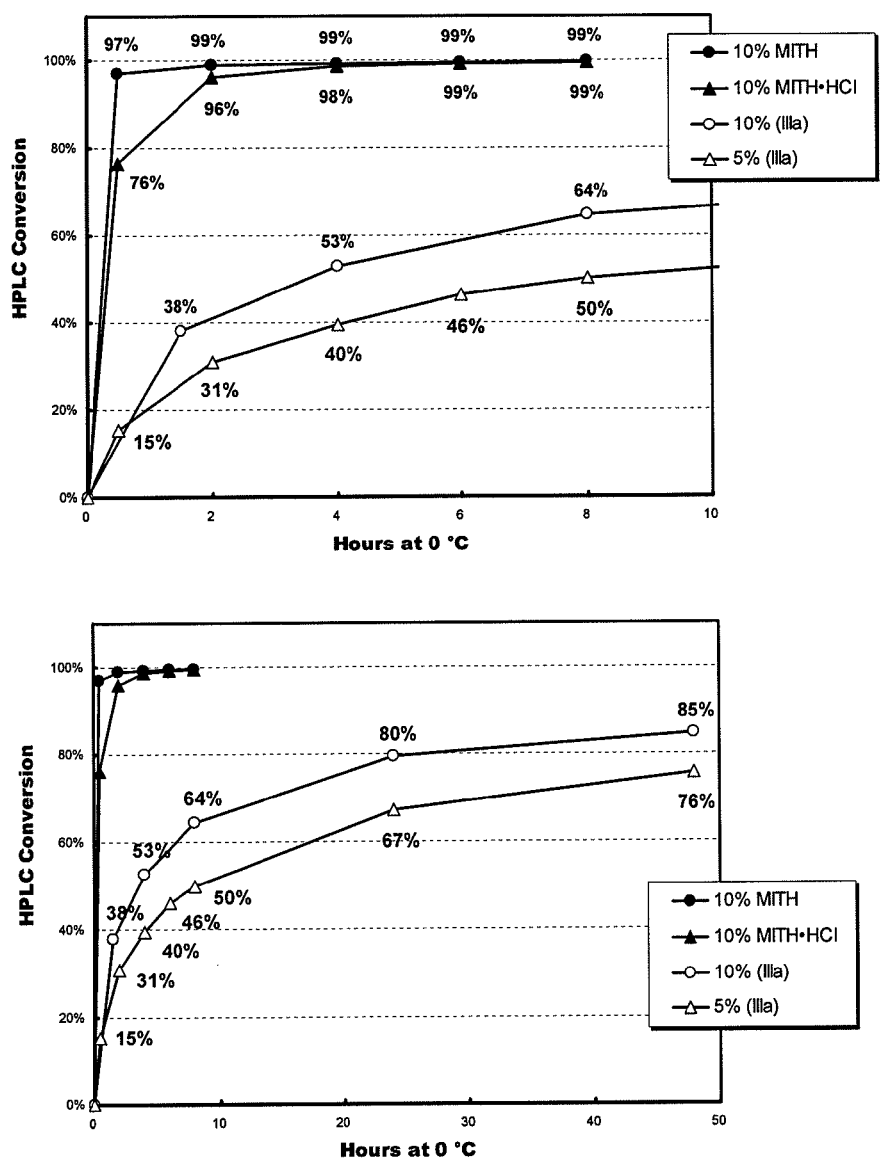
FIG. 8 shows the asymmetric conversion of benzaldehyde to addition reaction products, catalyzed by MITH, MITH•HCl and the disulfide of formula (IIIa), as assessed by HPLC.

MITH and certain related compounds were found to undergo this type of oxidation in air at ambient temperature. The instability of MITH under ambient conditions requires that it is stored under inert conditions, but this complicates transport, and reduces its utility for industrial applications. On the other hand, salt (Ib) and related salts of this invention demonstrate improved stability. For example, the purity of MITH (Ia), as assessed by HPLC, decreased from 93% to 81% when stored under ambient conditions for one month. Salt (Ib), however, showed no significant decrease in purity under the same conditions over the same period of time (FIG. 7).

The facile isolation of the catalyst salts of the compounds of formula (I) constitute an additional advantage. In particular, crude compounds of formula (I) can be obtained via aqueous work-up and filtration through silica gel. The crude material can then be directly contacted with HCl in a solvent such as isopropanol to form a solid salt (Is) in pure form that can be easily isolated by filtration. For example, the purity of MITH salt (Ib) isolated in this fashion was over 95% as judged by HPLC. Crude MITH (Ia), on the other hand, was only 24% pure, and would require isolation via chromatography in the absence of a salt formation operation.

The salts (Is) can be used directly for catalysis in asymmetric reactions. For example, the HCl salt (Ib) can be directly used for catalysis of asymmetric transformations without an impact on the asymmetric selectivity. The free-base compounds of formula (I) can also be regenerated prior to use in asymmetric reactions if necessary. Regeneration can be conducted by contacting a salt (Is) with a suitable base. For example, the HCl salt (Ib) can be converted to MITH (Ia) by treatment with aqueous base, such as sodium carbonate or sodium bicarbonate, and partitioned into a water-immiscible solvent such as n-heptane. Accordingly, the invention provides salt compounds that are not only easier to handle than the free-base compounds but that also allow for efficient isolation and purification as well as long-term storage. In contrast with MITH in particular, the inventive salts are easier to handle; are amenable to long term storage due to improved stability; allow for isolation of desired material via extraction from the crude product mixtures without column chromatography; and allow for purification by recrystallization.

The sulfonamides useful in the present invention may be synthesized according to a number of methods known in the art. In some embodiments, the sulfonamide of formula (II) is prepared by:

i) converting a compound of formula (IV)

(IV)

wherein Y is a leaving group, to a compound of formula (V)

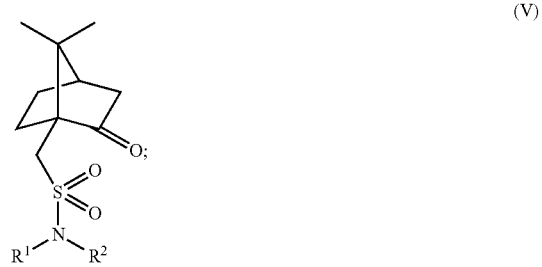

(V)

ii) converting the compound of formula (V), to a compound of formula (VI)

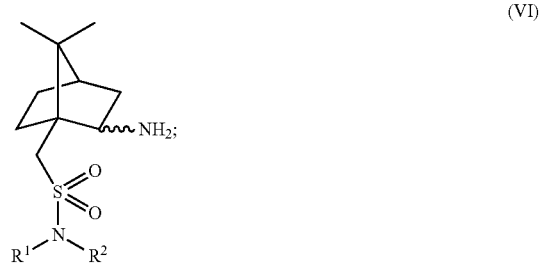

(VI)

and iii) converting the compound of formula (VI), to the sulfonamide of formula (II). This sulfonamide preparation procedure also applies to the enantiomers of (II), (IV), (V) and (VI). In some embodiments, $R^3$, $R^4$, and N together form a morpholine group. In some embodiments, at least one of $R^1$ and $R^2$ is a benzyl group or a substituted benzyl group. In some embodiments, the sulfonamide of formula (II) is the exo-diastereomer. In some embodiments, the sulfonamide of formula (II) is the endo-diastereomer. The sulfonamide of formula (II) can also be selected from the enantiomers of the exo- and endo-diastereomers:

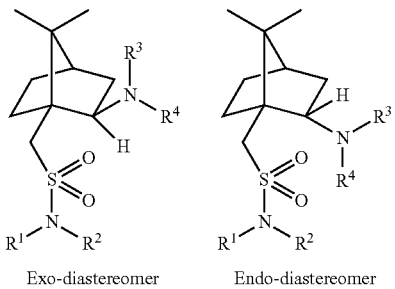

(II)

Exo-diastereomer    Endo-diastereomer

Compounds of formula (I) can also be accessed via a route including enamine intermediates. Accordingly, the present invention provides a process of for preparing a compound of formula (I)

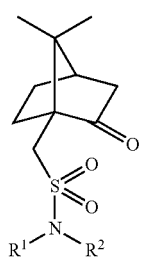

(I)

the process including:

i) converting a compound of formula (V)

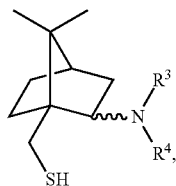

(V)

to an enamine compound of formula (VII)

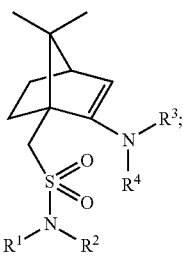

(VII)

and ii) converting the compound of formula (VII) to the compound of formula (I); wherein $R^1$ and $R^2$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl;

$R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl; or optionally $R^3$, $R^4$, and N can together form a $C_{3-10}$ heterocycle.

Figure 4:
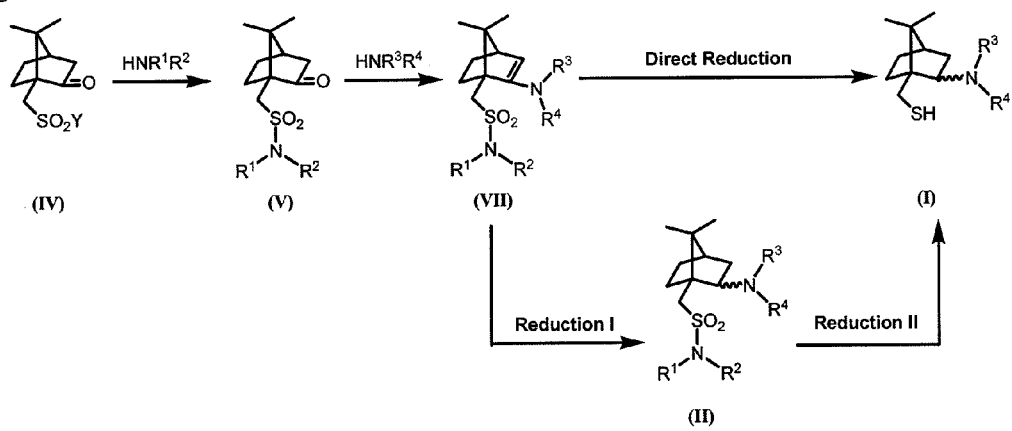
FIG. 4 shows the schematic for synthesis of MITH-type compounds of formula (I) via enamine compounds of formula (VII).

This "enamine route" also applies to the preparation of the enantiomers of (V), (VII) and (I). The synthetic method is illustrated in FIG. 4. The conversion of compound (VII) to compound (I) can be a one-step operation, a two-step operation, or a three-step operation. The two-step operation proceeds via a compound of formula (II). The three-step operation proceeds via a compound of formula (II) and a compound of formula (III), as described above. In some embodiments, the process further includes converting the compound of formula (VII) to a sulfonamide of formula (II). For example, enamines can be reduced to tertiary amines using reducing agents including, but not limited to, formic acid. Enamines can also be converted to tertiary amines via hydrogenation or transfer hydrogenation. Various methods for asymmetric enamine hydrogenation are known in the art, utilizing titanium-, rhodium-, and iridium-based catalysts as well as other catalysts. One of skill in the art will appreciate that other methods can be used to convert enamines of formula (VII) to the sulfonamides of formula (II).

The enamine route can provide any of the products and intermediates described above including their enantiomers. In some embodiments, $R^3$, $R^4$, and N together form a morpholine group. In some embodiments, at least one of $R^1$ and $R^2$ is a benzyl group or a substituted benzyl group. In some embodiments, the sulfonamide of formula (II) is the exo-diastereomer. In some embodiments, the sulfonamide of formula (II) is the endo-diastereomer. The sulfonamide of formula (II) can also be selected from the enantiomers of the exo- and endo-diastereomers. In some embodiments, the compound of formula (I) is selected from the group consisting of compound (Ia) and the enantiomer of compound (Ia), and the sulfonamide of formula (II) is selected from the group consisting of compound (IIa) and the enantiomer of compound (IIa). One of skill in the art will appreciate that if either of the compounds of formula (I) or (II) is present as a given enantiomer, then the other compound will have the same stereochemical configuration.

In some embodiments, the present invention provides a compound selected from compound (Is) and the enantiomer of compound (Is)

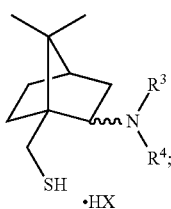

(Is)

wherein
$R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl; or optionally $R^3$, $R^4$, and N can together form a $C_{3-10}$ heterocycle; and HX is selected from the group consisting of an inorganic/mineral acid, a carboxylic acid, and an organic sulfonic acid.

In some embodiments, HX is HCl. In some embodiments, the compound of formula (Is) is selected from compound (Ib) and the enantiomer of (Ib).

In some embodiments, the inventions provides a compound selected from compound (III) and the enantiomer of compound (III)

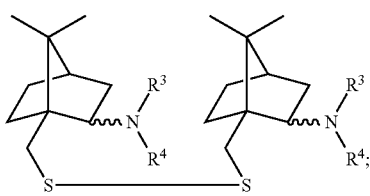

(III)

wherein
$R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl; or optionally $R^3$, $R^4$, and N can together form a C3-10 heterocycle.

In some embodiments, the compound of formula (III) is selected from compound (IIIa) and the enantiomer of compound (IIIa).

In some embodiments, the invention provides a compound selected from compound (XI) and the enantiomer of compound (XI) and compound (XI') and the enantiomer of compound (XI')

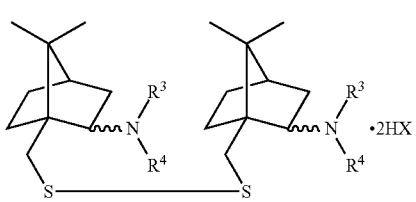

(XI)

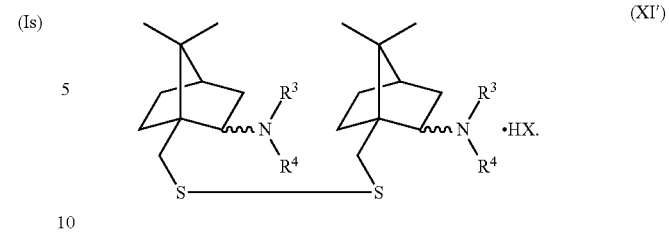

(XI')

In some embodiments, the compound of formula (XI) is selected from compound (IIIb) and the enantiomer of compound (IIIb) and compound (IIIb') and the enantiomer of compound (IIIb')

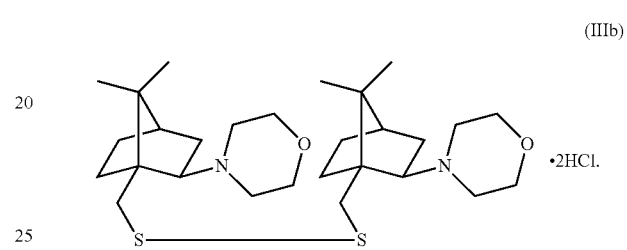

(IIIb)

In some embodiments, the present invention provides a method of asymmetric synthesis. The method including contacting a compound selected from (Is), (Ib), (III), (IIIa), (XI), (IIIb), and their enantiomers with reactants in an asymmetric transformation to stereoselectively provide a product. In some embodiments, the asymmetric transformation is an asymmetric addition reaction. In some embodiments, the reactants include a compound of formula (VIII)

(VIII)

and a compound of formula (IX)

$R^7ZnR^8$     (IX);

and
the products include a compound of formula (X)

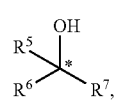

(X)

wherein
$R^5$ is aryl, alkyl, alkenyl or alkynyl;
$R^6$ is H, methyl, trifluoromethyl or $CO_2R^9$, wherein $R^9$ is alkyl; and
$R^7$ and $R^8$ are independently aryl, alkyl, alkenyl, or alkynyl.

In general, the asymmetric addition reaction is conducted such that the catalyst compounds of this invention act as ligands to form coordination complexes with organozinc compounds (IX) prior to reaction with carbonyl compounds (VIII). Salts (Is), disulfides (III), and salts of disulfides (XI) or (XI') can all be used as catalysts in the asymmetric addition reactions of the present invention. Any suitable molar ratio of the catalyst to organozinc compound (IX) can be employed in the asymmetric addition reactions. In some cases, a stoichiometric amount of the catalyst can be used. In other cases, less than one equivalent of the catalyst can be used for each equivalent of organozinc compound used. The minimum amount of the catalyst relative to other reactants may depend on the structure of the catalyst, the specific carbonyl compound and organozinc compound to be reacted, the reaction conditions, and the maximum time allowed for completion of the reaction. Appropriate catalyst loading can be readily determined by one of skill in the art. The chiral alcohol product (X) has, in general, a stereomeric excess greater than zero. For example, the chiral alcohol can be formed in at least about 50% stereomeric excess, or at least about 60%, or at least about 70%, or at least about 80%, or at least about 90%. The stereomeric excess refers to the chirality at the hydroxyl-bearing carbon of the alcohol group generated by the addition reaction. When the carbonyl compound (VIII) is achiral, the chiral alcohol can be one of two enantiomers, and enantiomeric excess (e.e.) is the measure of stereomeric excess. When the carbonyl compound (VIII) is already chiral, the chiral alcohol product is a diastereomer, and diastereomeric excess (d.e.) is the formally appropriate measure of stereomeric excess.

For example, MITH (Ia) and MITH salt (Ib) catalyze the asymmetric 1,2-addition of ethane from diethylzinc to benzaldehyde (Table 1). Both MITH and MITH•HCl showed comparable catalytic activity and provided products with identical optical purity (compare Table 1, entries 1 and 3, with Table 1, entries 2 and 4). The apparent retention of selectivity upon catalyst salt formation was unexpected, given that the chloride counter ion has been shown to interfere with asymmetric catalysis using aminothiol compounds as ligands in certain situations (see, for example H of, R. P. Ph.D. Dissertation, University of Groningen, The Netherlands, 1995). MITH and related compounds can be regenerated from salts by treatment with aqueous base, such as sodium carbonate or sodium bicarbonate, and partitioned into a water immiscible solvent such as n-heptane. Regenerated MITH (Ia), for example, provides addition products with the same optical purity as those provided by free-base MITH (without salt formation) and the MITH salt (Table 1, entries 5, 3, and 4, respectively).

As discussed above, the disulfides of formula (III) or their salts (XI) and (XI') can also be employed as catalysts or stoichiometric reagents in asymmetric C—C bond forming reactions. Such transformations are useful for the manufacture of drugs and drug intermediates, among other industrially relevant compounds. Disulfide (IIIa), for example, is also an asymmetric catalyst. Disulfide (IIIa) catalysed the asymmetric 1,2-addition of an ethyl group from diethylzinc to benzaldehyde (Table 1, entry 6). This catalyst provided products with optical purity comparable to those provided by free-base MITH and its HCl salt (Table 1, entries 3 and 4, respectively). The novel disulfides of formula (III) can also be converted to salts (XI) and (XI') using suitable acids. Examples of suitable acids including carboxylic acids (trifluoroacetic acid and the like), organic sulfonic acids (methanesulfonic acid, trifluoromethanesulfonic acid, p-toluenesulfonic acid and the like), and inorganic/mineral acids (hydrochloric acid, hydrobromic acid, hydroiodic acid, phosphoric acid, sulfuric acid, and the like). These salts can also be employed in the asymmetric reactions of the invention.

The catalytic activity of disulfide (IIIa) was confirmed using NMR spectroscopy. A 1,2-addition reaction of ethyl group from diethylzinc to benzaldehyde using 20 mol % of (IIIa) as the catalyst was conducted. $^1$H NMR spectroscopic analysis of the crude reaction product revealed a binary mixture of 1-phenyl-propanol and disulfide (IIIa), containing no detectable MITH. Moreover, the catalyst (IIIa) was recovered in 98% yield after isolation by column chromatography. Together, these results indicate that disulfide (IIIa) is the catalytic species, ruling out the possibility that the disulfide was converted to a free zinc thiolate upon contact with diethylzinc. The new disulfide compounds of formula (IIIa) can also be used for arylzinc addition reactions (see, for example, Table 1, entry 7). Benzaldehyde was smoothly converted to diarylmethanol in 96% e.e.; the same optical purity was observed for MITH catalysis as reported in *J. Org. Chem.* 2006, 71, 833-835.

TABLE 1

Asymmetric organozinc addition to aldehydes

| Entry | X | Catalyst[a] | R | EtRZn | Temp. | Time | Yield | Optical Purity[c] |
|---|---|---|---|---|---|---|---|---|
| 1 | H | MITH | Et[b] | 1.5 eq. | rt. | 4 h | 82% | 93.6% e.e. |
| 2 | H | MITH•HCl | Et | 1.6 eq. | rt. | 4 h | 89% | 92.3% e.e. |
| 3 | H | MITH | Et | 1.5 eq. | 0° C. | 17 h | 87% | 96.2% e.e. |
| 4 | H | MITH•HCl | Et | 1.6 eq. | 0° C. | 17 h | 80% | 96.3% e.e. |
| 5 | H | MITH[d] | Et | 1.5 eq. | 0° C. | 16 h | 85% | 96.3% e.e. |
| 6 | H | 5 mol % (IIIa) | Et | 1.6 eq. | 0° C. | 17 h | 81% | 95.2% e.e. |
| 7 | Me | (IIIa) | Ph[e] | Et$_2$Zn (2.0 eq.) PhEtZn (2.0 eq.) | 0° C. | 24 h | 74% | 95.9% e.e. |

[a]Unless otherwise specified, 10 mol % catalyst was used.
[b]Et$_2$Zn was used as a 1.0M solution in hexanes.
[c]The e.e. values were determined by normal phase chiral HPLC.
[d]The catalyst was prepared in situ from MITH•HCl: The MITH•HCl was extracted between n-heptane and 1M aq. Na$_2$CO$_3$ (10 mL) to regenerate MITH free base. The organic solution was washed with 10% aq. NaCl (5 mL), concentrated and co-evaporated once with n-heptane (10 mL) to give a colorless oil directly for the catalytic reaction.
[e]The mixed zinc reagent was prepared according to literature procedures (*J. Org. Chem.* 2006, 71, 833-835); see example 10 for details.

EXAMPLES

The symbols, conventions and abbreviations used in the above specification and in the following examples are consistent with those used in the contemporary scientific literature, for example, *Journal of the American Chemical Society* and *The ACS Style Guide: effective communication of scientific information*, 3rd ed.; Coghill, A. M. and Garson, L. R. ed.; Washington, D.C., Oxford University Press, New York Oxford, 2006.

t-Bu—tert-butyl
Me—methyl
Et—ethyl
Pr—propyl
Ph—phenyl ($C_6H_5$)
g—gram(s)
mg—milligram(s)
mL—milliliter(s)
M—molarity
N—normality
MHz—megahertz
mol—mole(s)
mmol—millimole(s)
min—minute(s)
h—hour(s)
TLC—thin layer chromatography
IPA—isopropanol
DCM—dichloromethane
DMAC—N,N-dimethylacetamide
THF—tetrahydrofuran
brine—saturated aqueous sodium chloride solution
AcOH—acetic acid
HPLC—High performance liquid chromatography The following examples are provided to further illustrate, but not to limit this invention.

Example 1

Synthesis of the Disulfide of Formula (IIIa)

(1S,4R)—N-Benzyl-10-camphorsulfonamide (Va)

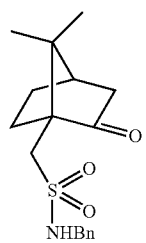

(Va)

A solution of camphorsulfonyl chloride (80.1 g, 0.32 mol) in dichloromethane (DCM, 160 mL) was added dropwise to a solution of benzylamine (87.5 mL, 0.80 mol) in DCM (240 mL). The addition was conducted at <20° C., and the mixture was subsequently stirred at ambient temperature. Following reaction completion as judged by HPLC analysis, the mixture was diluted with DCM (240 mL) and 3 N aq. HCl (640 mL). After stirring for 0.5 h the layers were separated and the organic layer was washed with 1 M aq. $Na_2CO_3$ (400 mL) and brine (400 mL). DCM was evaporated to yield an orange oil. The oil was used without further purification. The proton and carbon NMR spectra were identical to reported data (*Tetrahedron: Asymmetry* 1997, 8, 2479-2496).

(1S,4R)—N-Benzyl-2-hydroxyimino-7,7-dimethyl-bicyclo[2.2.1]hept-1-ylmethanesulfonamide (IXa)

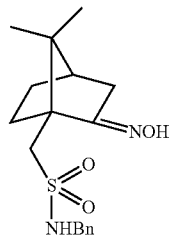

(IXa)

To a solution of (1S,4R)—N-benzyl-10-camphorsulfonamide (Va) in ethanol (320 mL) was added sodium acetate (39.4 g, 480 mmol) and $NH_2OH \cdot HCl$ (33.4 g, 481 mmol). The reaction mixture was heated under gentle reflux until the reaction was complete as judged by TLC. The hot solution was filtered and the solids were washed with ethanol (80 mL). After the filtrate was cooled to ambient temperature, water (800 mL) was added dropwise to the combined filtrates. After stirring at ambient temperature for an hour, the product mixture was filtered and the filter cake was washed with an ethanol/water mixture (1:2, 240 mL) and dried in vacuo to give a white powder (105.9 g, 315 mmol, 98% for two steps, >99.9% HPLC purity). The proton and carbon NMR spectra were identical to reported data (*Tetrahedron: Asymmetry* 2000, 11, 1629-1644).

(1S,2R,4R)—N-Benzyl-2-amino-7,7-dimethylbicyclo[2.2.1]hept-1-ylmethanesulfonamide (VIa)

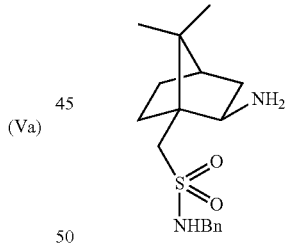

(VIa)

A solution of (1S,4R)—N-benzyl-2-hydroxyimino-7,7-dimethylbicyclo[2.2.1]hept-1-ylmethanesulfonamide (IXa) (45.0 g, 134 mmol) in ethanol (360 mL) was added dropwise to a solution of sodium acetate (94.5 g, 1150 mmol) and $TiCl_3$ (460 mmol) in 10.5% wt. aq. HCl (320 mL) at −20 to −10° C. The addition was conducted below 0° C., and the reaction mixture was then stirred at 0° C. for an hour prior to addition of neat $t$-$BuNH_2 \cdot BH_3$ (29.1 g, 335 mmol) in portions. The mixture was stirred at 0-10° C. for 30 minutes and then at ambient temperature. After the reaction was completed, the solution was diluted with ethyl acetate (675 mL) and was extracted with water (450 mL). Following separation of the layers, the organic layer was washed with sat. aq. $NH_4Cl$ (675 mL), 1 M aq. $Na_2CO_3$ (900 mL) and finally with 10% aq. NaCl (450 mL). The organic solution was concentrated to give the crude amine product (1S,2R,4R)—N-benzyl-2- amino-7,7-dimethylbicyclo[2.2.1]hept-1-ylmethanesulfonamide (VIa) as light yellow powder. The crude product was dissolved in ethanol (180 mL) at 70-75° C. and was hot-filtered. The filter cake was washed with hot ethanol (45 mL), and the filtrate was slowly cooled allowing recrystallization to occur at about 50° C. After stirring for an hour at 0° C., the white suspension was filtered and washed with cold ethanol (45 mL) to give pure (1S,2R,4R)—N-benzyl-2-amino-7,7-dimethylbicyclo[2.2.1]hept-1-ylmethanesulfonamide (VIa) as a white powder (23.5 g; 54%; >99.9% pure as assessed by HPLC).

$^1$H NMR δ (400 MHz, CDCl$_3$) 7.39-7.31 (m, 5H), 5.05 (br, 1H), 4.37 (d, J=14.2 Hz, 1H), 4.32 (d, J=14.2 Hz, 1H), 3.49 (d, J=13.6 Hz, 1H), 3.27 (dd, J=8.8, 5.2 Hz, 1H), 2.76 (d, J=14.0 Hz, 1H), 1.82-1.70 (m, 4H), 1.55-1.46 (m, 4H), 1.19-1.15 (m, 1H), 0.98 (s, 3H), 0.76 (s, 3H). ESI MS Calculated for [C$_{17}$H$_{26}$N$_2$O$_2$SNa+]=345.1607. Found: 345.1611

(1S,2R,4R)—N-Benzyl-2-morpholino-7,7-dimethyl-bicyclo[2.2.1]hept-1-ylmethanesulfonamide (IIa)

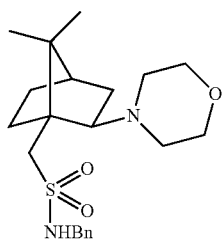

(IIa)

Bis(2-bromoethyl)ether (18.3 mL, 146 mmol) was added to a solution of (1S,2R,4R)—N-benzyl-2-amino-7,7-dimethylbicyclo[2.2.1]hept-1-ylmethanesulfonamide (VIa) (23.5 g, 72.9 mmol) and N,N-Diisopropylethylamine (DIPEA) (55.8 mL, 320 mmol) in N,N-dimethylacetamide (DMAC) (470 mL). The solution was heated at 120° C. until the amine (1S,2R,4R)—N-benzyl-2-amino-7,7-dimethylbicyclo[2.2.1]hept-1-ylmethanesulfonamide (VIa) was <2% by HPLC analysis. The mixture was cooled to ambient temperature and diluted with toluene (470 mL) and was extracted with water (470 mL). After layer separation, the toluene layer was washed twice with 10% aq. NaCl (230 mL each) and concentrated to give the crude product as a brown solid. The sulfonamide (1S,2R,4R)—N-benzyl-2-morpholino-7,7-dimethylbicyclo[2.2.1]hept-1-ylmethanesulfonamide (IIa) was crystallized from a mixture of toluene (23 mL) and n-heptane (47 mL) by slowly cooling from 75° C. to 60° C., stirring at 60° C. for an hour and then cooling to ambient temperature, followed by the addition of n-heptane (70 mL) and stirring for an hour. The suspension was filtered and the powder was washed with a mixture of toluene and n-heptane (1:5, 47 mL) to give (1S,2R,4R)—N-benzyl-2-morpholino-7,7-dimethylbicyclo[2.2.1]hept-1-ylmethanesulfonamide (IIa) as an orange to light brown powder (22.2 g; 78%; 98.9% pure as assessed by HPLC).

$^1$H NMR δ (400 MHz, CDCl$_3$) 7.41-7.31 (m, 5H), 4.99 (t, J=6.2 Hz, 1H), 4.36 (dd, J=13.8, 6.2 Hz, 1H), 4.30 (dd, J=13.8, 5.8 Hz, 1H), 3.78 (d, J=14.8 Hz, 1H), 3.65 (ddd, J=11.2, 6.4, 2.8 Hz, 2H), 3.58 (ddd, J=11.2, 6.0, 3.2 Hz, 2H), 2.88 (d, J=14.8 Hz, 1H), 2.71-2.57 (m, 5H), 2.15 (dd, J=12.3, 12.3, 4.9 Hz, 1H), 1.98-1.91 (m, 1H), 1.83-1.74 (m, 1H), 1.71 (dd, J=4.4 Hz, 1H), 1.56 (ddd, J=12.8, 9.5, 3.5 Hz, 1H), 1.46 (dd, J=13.0, 9.4 Hz, 1H), 1.20 (ddd, J=12.5, 9.3, 4.9 Hz, 1H), 0.87 (s, 3H), 0.78 (s, 3H). ESI MS Calculated for [C$_{21}$H$_{32}$N$_2$O$_3$SNa$^+$]=415.2026. Found: 415.2028

(1S,2R,4R)-1,2-bis((7,7-dimethyl-2-morpholinobicyclo[2.2.1]heptan-1-yl)methyl)disulfane (IIIa)

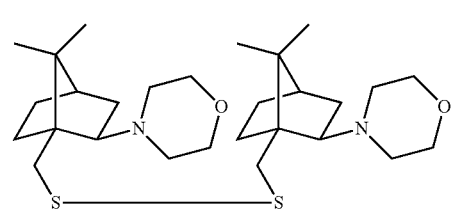

(IIIa)

To a solution of (1S,2R,4R)—N-Benzyl-2-morpholino-7,7-dimethylbicyclo[2.2.1]hept-1-ylmethanesulfonamide (IIa) (10.07 g, 25.7 mmol) in toluene (70 mL) was added sodium bis(2-methoxyethoxy)aluminum hydride (73 mL, 70% wt. in toluene, 256 mmol) and the resulting solution was heated to reflux. After the reaction was complete as judged by HPLC, the mixture was cooled to 0° C. and THF (140 mL), water (10 mL), diatomaceous earth, 15% aq. NaOH (10 mL), water (26 mL) and Na$_2$SO$_4$ were added sequentially. The suspension was stirred at ambient temperature for about one hour. The mixture was filtered through diatomaceous earth and the filter cake was washed twice with THF (140 mL each). The filtrate was concentrated and the residue was diluted with ethyl acetate (200 mL) and was washed with 10% aq. NaCl (100 mL×3) and brine (50 mL) and concentrated to give the crude disulfide as a light brown semi-solid, which was used directly in the next step.

$^1$H NMR δ (400 MHz, CDCl$_3$) 3.76 (ddd, J=11.0, 6.6, 2.6 Hz, 4H), 3.63 (ddd, J=11.0, 6.6, 3.0 Hz, 4H), 3.25 (d, J=12.0 Hz, 2H), 2.80 (d, J=11.6 Hz, 2H), 2.73-2.69 (m, 4H), 2.58-2.54 (m, 4H), 2.32 (dd, J=9.2, 6.0 Hz, 2H), 1.94-1.90 (m, 2H), 1.72-1.64 (m, 4H), 1.36 (dd, J=12.8, 9.2 Hz, 2H), 1.25-1.16 (m, 4H), 1.09-1.05 (m, 2H), 0.874 (s, 6H), 0.866 (s, 6H). ESI MS Calculated for [C$_{28}$H$_{48}$N$_2$O$_2$S$_2$Na$^+$]=531.3049. Found: 531.3058. MS/MS (m/e): 254.2, 509.5.

Example 2

Synthesis of MITH•HCl (Ib)

(1S,2R,4R)-(7,7-dimethyl-2-morpholinobicyclo[2.2.1]heptan-1-yl)methanethiol, (−)-2-exo-morpholinoisoborne-10-thiol (MITH; (Ia))

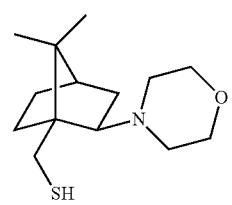

(Ia)

To a solution of the crude disulfide (1S,2R,4R)-1,2-bis((7,7-dimethyl-2-morpholinobicyclo[2.2.1]heptan-1-yl)methyl)disulfane (IIIa) in acetic acid (20 mL) and THF (40 mL) was added zinc dust (8.4 g, 128 mmol). The mixture was heated at 60° C. until the reaction was complete as judged by HPLC. The mixture was then cooled to ambient temperature and diluted with ethyl acetate (60 mL). The pH of the suspension was increased to about 6-7 with 20% aq. Na$_2$CO$_3$ (50 mL), and diatomaceous earth was added and the mixture was filtered through further diatomaceous earth. The filter cake was washed with ethyl acetate (100 mL). The filtrate was mixed with water (100 mL), and the organic layer was washed with 10% aq. Na$_2$CO$_3$ (100 mL), 10% aq. NaCl (100 mL), and brine (50 mL). The organic layer was concentrated to give crude (1S,2R,4R)-(7,7-dimethyl-2-morpholinobicyclo[2.2.1]heptan-1-yl)methanethiol, (−)-2-exo-morpholinoisoborne-10-thiol (MITH; (Ia)) as a yellow oil that was used directly in the next step. The proton NMR spectrum was identical to reported data (*J. Org. Chem.* 2006, 71, 833-835).

$^1$H NMR δ (400 MHz, CDCl$_3$) 3.73 (ddd, J=11.1, 6.3, 3.1 Hz, 2H), 3.65 (ddd, J=11.2, 6.0, 3.2 Hz, 2H), 2.88 (dd, J=13.4, 7.8 Hz, 1H), 2.68-2.57 (m, 5H), 2.46 (dd, J=9.2, 6.0 Hz, 1H), 1.97-1.90 (m, 1H), 1.76-1.67 (m, 2H), 1.61-1.53 (m, 2H), 1.44-1.32 (m, 2H), 1.14-1.07 (m, 1H), 0.92 (s, 3H), 0.88 (s, 3H).

(1S,2R,4R)-(7,7-dimethyl-2-morpholinobicyclo[2.2.1]heptan-1-yl)methanethiol hydrochloride (MITH•HCl; (Ib))

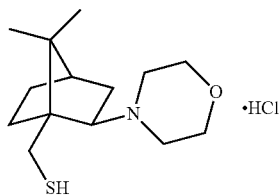

(Ib)

A solution of crude (1S,2R,4R)-(7,7-dimethyl-2-morpholinobicyclo[2.2.1]heptan-1-yl)methanethiol, (−)-2-exo-morpholinoisoborne-10-thiol (MITH; (Ia)) in ethyl acetate (50 mL) was filtered through a 1-cm pad of silica gel, and the pad of silica gel was washed once with ethyl acetate (100 mL). The filtrate was concentrated and the resulting oil (4.34 g, 24.0% HPLC purity) was diluted with isopropanol (IPA) (13 mL) and n-heptane (22 mL). A solution of HCl in IPA (22 mL, 73 mmol) was added dropwise to the solution and the resulting suspension was dissolved by heating to 69-71° C. The solution was gently cooled to 35° C., then kept at this temperature for an hour, after which time n-heptane (13 mL, 3 vol.) was added. The suspension was then cooled to ambient temperature and was stirred for about 1 hour. The mixture was filtered and the filter cake was washed with a mixture of IPA and n-heptane (1:2, 13 mL) providing (1S,2R,4R)-(7,7-dimethyl-2-morpholinobicyclo[2.2.1]heptan-1-yl)methanethiol hydrochloride (Ib) as a white powder (1.65 g; 22%; 95.5% pure as assessed by HPLC).

$^1$H NMR δ (400 MHz, DMSO-d$_6$) 9.80 (s, 1H, br), 4.28-4.12 (m, 2H), 3.91-3.81 (m, 3H), 3.54-3.49 (m, 2H), 3.37-3.28 (m, 2H), 3.15-3.06 (m, 1H), 2.84-2.77 (m, 2H), 2.25-2.22 (m, 1H), 1.80-1.65 (m, 4H), 1.40-1.35 (m, 1H), 1.17-1.09 (m, 1H), 0.98 (s, 3H), 0.89 (s, 3H).

Example 3

Synthesis of MITH (Ia)

(1S,2R,4R)-(7,7-dimethyl-2-morpholinobicyclo[2.2.1]heptan-1-yl)methanethiol, (−)-2-exo-morpholinoisoborne-10-thiol (MITH; (Ia))

Crude (1S,2R,4R)-(7,7-dimethyl-2-morpholinobicyclo[2.2.1]heptan-1-yl)methanethiol, (−)-2-exo-morpholinoisoborne-10-thiol (MITH; (Ia)) was prepared as in example 2 (from 5.04 g, 12.8 mmol, of (1S,2R,4R)—N-Benzyl-2-morpholino-7,7-dimethylbicyclo[2.2.1]hept-1-ylmethanesulfonamide (IIa) and was purified by silica gel column chromatography using ethyl acetate/n-heptane (1:20) as the eluent to give a colorless oil (2.32 g; 71% yield for two steps). (1S,2R,4R)-(7,7-Dimethyl-2-morpholinobicyclo[2.2.1]heptan-1-yl)methanethiol, (−)-2-exo-morpholinoisoborne-10-thiol (MITH) was substantially pure as assessed by NMR.

Example 4

Synthesis of (IIIb)

(1S,2R,4R)-1,2-bis((7,7-dimethyl-2-morpholinobicyclo[2.2.1]heptan-1-yl)methyl)disulfane hydrochloride (IIIb)

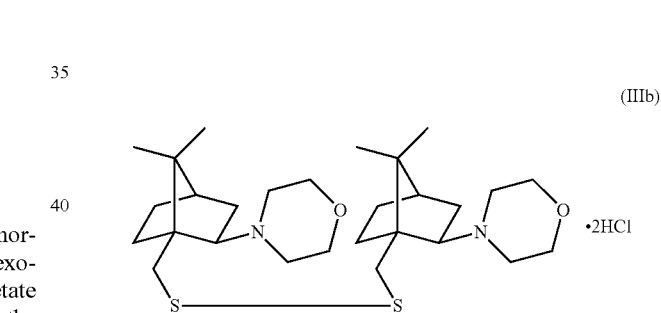

(IIIb)

To a solution (1S,2R,4R)-1,2-bis((7,7-dimethyl-2-morpholinobicyclo[2.2.1]heptan-1-yl)methyl)disulfane (IIIa) (111 mg, 0.22 mmol) in IPA (1 mL) and n-heptane (2 mL) was added a solution of HCl in IPA (1 mL, 4.9 mmol). The resulting mixture was concentrated in vacuo to give the title product (1S,2R,4R)-1,2-bis((7,7-dimethyl-2-morpholinobicyclo[2.2.1]heptan-1-yl)methyl)disulfane hydrochloride (IIIb) as a white powder.

$^1$H NMR δ (400 MHz, CD$_3$OD) 4.50-4.45 (m, 2H), 4.29-4.24 (m, 1H), 4.05-3.96 (m, 3H), 3.70-3.67 (m, 1H), 3.59-

3.55 (m, 2H), 3.29-3.20 (m, 2H), 2.40-2.36 (m, 1H), 1.96-1.83 (m, 4H), 1.49-1.44 (m, 1H), 1.34-1.24 (m, 1H), 1.08 (s, 3H), 1.03 (s, 3H).

Example 5

Synthesis of morpholino-(1S,4R)-(7,7-dimethyl-2-morpholinobicyclo-[2.2.1]heptan-1-yl)methanesulfonamide (IIc)

Morpholino-(1S,4R)-(7,7-dimethyl-2-morpholinobicyclo[2.2.1]hept-2-en-1-yl)methanesulfonamide (VIIc)

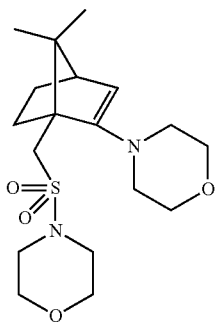

(VIIc)

A reaction vessel was charged with morpholino-(1S,4R)-10-camphorsulfonamide (10.0 g, 33.2 mmol), toluene (130 mL), and morpholine (28.6 mL, 332 mmol). The mixture was heated to 60° C. and a solution of TiCl$_4$ (7.3 mL, 66.6 mmol) in toluene (70 mL) was added dropwise over a 10 minute period. The mixture was then stirred under gentle reflux for 22 hours and was then cooled to ambient temperature. The suspension was filtered through diatomaceous earth, and the filter cake was washed twice with toluene (100 mL each) providing the pure enamine morpholino-(1S,4R)-(7,7-dimethyl-2-morpholinobicyclo[2.2.1]hept-2-en-1-yl)methanesulfonamide (VIIc) as a solution in toluene. The enamine was used directly in the next reduction step.

$^1$H NMR δ (400 MHz, CDCl$_3$), 5.12 (d, J=3.6 Hz, 1H), 3.83 (dd, J=4.6, 4.6 Hz, 4H), 3.76 (dd, J=4.8, 4.8 Hz, 4H), 3.52 (d, J=15.2 Hz, 1H), 3.36-3.26 (m, 4H), 3.08-3.02 (m, 2H), 2.75 (d, J=14.8 Hz, 1H), 2.52-2.47 (m, 3H), 2.28 (dd, J=3.6, 3.6 Hz, 1H), 2.01-1.94 (m, 1H), 1.53 (ddd, J=12.3, 9.1, 3.5 Hz, 1H), 1.23-1.17 (m, 1H), 0.923 (s, 3H), 0.861 (s, 3H).

Morpholino-(1S,4R)-(7,7-dimethyl-2-morpholinobicyclo[2.2.1]heptan-1-yl)methanesulfonamide (IIc)

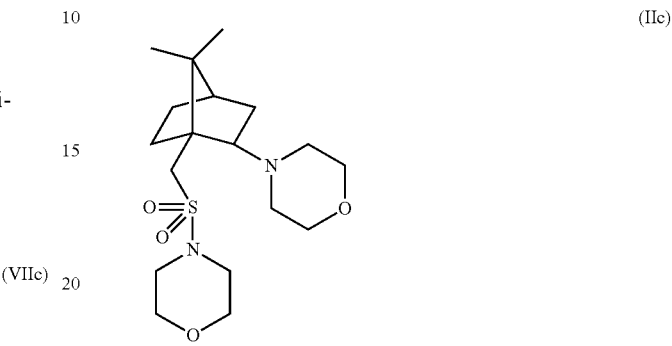

(IIc)

A solution of formic acid (5.2 g, 113 mmol) in DCM (50 mL) was slowly added to a solution of enamine morpholino-(1S,4R)-(7,7-dimethyl-2-morpholinobicyclo[2.2.1]hept-2-en-1-yl) methanesulfonamide (VIIc) (32 g, 86.4 mmol) in DCM (160 mL) at 0 to 10° C. The reaction mixture was stirred at ambient temperature for 4 hours and was quenched by addition of 0.4 N aq. HCl (250 mL). After separation of layers, the aqueous layer was brought to pH 8-9 by 30% aq. NaOH. The solution was extracted with DCM (300 mL), and the DCM solution was collected, dried over anhydrous MgSO$_4$, and concentrated to give the crude product morpholino-(1S,4R)-(7,7-dimethyl-2-morpholinobicyclo[2.2.1]heptan-1-yl) methanesulfonamide (IIc) as a solid (20.4 g, 63%; 95.7% pure as assessed by GC).

Example 6

Representative diethylzinc addition reaction catalyzed by (1S,2R,4R)-(7,7-dimethyl-2-morpholinobicyclo[2.2.1]heptan-1-yl)methanethiol hydrochloride (MITH•HCl; (Ib))

After stirring a mixture of (1S,2R,4R)-(7,7-dimethyl-2-morpholinobicyclo[2.2.1]heptan-1-yl)methanethiol hydrochloride (MITH•HCl; (Ib)) (58 mg, 0.20 mmol) and diethylzinc solution (3.2 mmol, 1.0 M in hexanes) at ambient temperature for 30 minutes, neat benzaldehyde (200 µL, 2.0 mmol) was added in one portion at 0° C. Upon completion of the reaction (as judged by TLC analysis), sat. aq. NH$_4$Cl (3 mL) was slowly added to the reaction product mixture followed by ethyl acetate (20 mL). The mixture was washed twice with 1 N aq. HCl (20 mL each) and brine (5 mL), dried over solid Na$_2$SO$_4$, and concentrated to give a colorless oil which was purified by silica gel column chromatography (1:10 ethyl acetate/n-heptane) to give (R)-1-phenyl-propanol as a colorless oil (217 mg; 80%; 96.3% e.e.). The optical purity was determined by normal phase HPLC using a Chiralcel OD-H chiral column (eluted with isocratic IPA/Hexane=2:98, with 1.0 mL/minute flow rate; monitoring at 254 nm).

Example 7

Representative Diethylzinc Addition Reaction Catalyzed by (1S,2R,4R)-(7,7-dimethyl-2-morpholinobicyclo[2.2.1]heptan-1-yl)methanethiol, (−)-2-exo-morpholinoisoborne-10-thiol (MITH; (Ia)) prepared from (1S,2R,4R)-(7,7-dimethyl-2-morpholinobicyclo[2.2.1]heptan-1-yl)methanethiol hydrochloride (MITH•HCl; (Ib))

A solution of (1S,2R,4R)-(7,7-dimethyl-2-morpholinobicyclo[2.2.1]heptan-1-yl)methanethiol hydrochloride (MITH•HCl; (Ib)) (58 mg, 0.20 mmol) in n-heptane (10 mL) was extracted with 1 M $Na_2CO_3$ (10 mL). After separation of layers, the n-heptane layer was washed with 10% aq. NaCl (5 mL) and concentrated. The residual oil was co-evaporated with n-heptane (10 mL) to give MITH free base as a colorless oil. To the oil was added diethylzinc (3.0 mmol, 1.0 M in hexanes) at ambient temperature, and the mixture was stirred for 10 minutes. Neat benzaldehyde (200 μL, 2.0 mmol) was added in one portion at 0° C. Upon complete consumption of benzaldehyde as judged by TLC, sat. aq. $NH_4Cl$ (3 mL) was slowly added to the reaction product mixture followed by ethyl acetate (20 mL). The mixture was washed twice with 1 N aq. HCl (20 mL each) and brine (5 mL), dried over solid $Na_2SO_4$ and concentrated to give a colorless oil which was purified by silica gel column chromatography (1:10 ethyl acetate/n-heptane) to give (R)-1-phenyl-propanol as a colorless oil (232 mg; 85%; 96.3% e.e.).

Example 8

Representative diethylzinc addition reaction catalyzed by (1S,2R,4R)-1,2-bis((7,7-dimethyl-2-morpholinobicyclo[2.2.1]heptan-1-yl)methyl)disulfane (IIIa)

After stirring a mixture of (1S,2R,4R)-1,2-bis((7,7-dimethyl-2-morpholinobicyclo[2.2.1]heptan-1-yl)methyl)disulfane (IIIa) (51 mg, 0.10 mmol) and diethylzinc (3.2 mmol, 1.0 M in hexanes) at ambient temperature for 30 minutes, neat benzaldehyde (200 μL, 2.0 mmol) was added in one portion. Upon complete consumption of benzaldehyde as judged by TLC, sat. aq. $NH_4Cl$ (3 mL) was slowly added to the reaction product mixture followed by ethyl acetate (20 mL). The mixture was washed twice with 1 N aq. HCl (20 mL each) and brine (5 mL), dried over solid $Na_2SO_4$, and concentrated to give a colorless oil which was purified by silica gel column chromatography (1:10 ethyl acetate/n-heptane) to give (R)-1-phenyl-propanol as a colorless oil (221 mg; 81%; 95.2% e.e.).

Example 9

Representative propargylzinc addition reaction catalyzed by (1S,2R,4R)-1,2-bis((7,7-dimethyl-2-morpholinobicyclo[2.2.1]heptan-1-yl)methyl)disulfane (IIIa)

To a solution of (1S,2R,4R)-1,2-bis((7,7-dimethyl-2-morpholinobicyclo[2.2.1]heptan-1-yl)methyl)disulfane (IIIa) (51 mg, 0.10 mmol) and THF (0.66 mL) was added dimethylzinc (3.3 mL, 4.0 mmol, 1.2 M in toluene) and phenylacetylene (0.44 mL, 4.0 mmol). After stirring at ambient temperature for two hours, the solution was cooled to 0° C. Neat benzaldehyde (0.10 mL, 1.0 mmol) was added in one portion and the reaction was stirred at 0° C. for 2 days. The reaction was quenched by addition of sat. aq. $NH_4Cl$ (3 mL) slowly and then diluted with DCM (20 mL) and 1 N aq. HCl (15 mL). After separation of layers, the aqueous solution was washed twice with DCM (10 mL). The DCM layers were combined, dried over solid $Na_2SO_4$, and concentrated to give a light yellow oil which was purified by silica gel column chromatography (1:5 ethyl acetate:n-heptane) to give (1S)-1,3-diphenyl-prop-2-yn-1-ol as a pale yellow oil (80 mg; 38%; 18.2% e.e.). The optical purity was determined by normal phase HPLC using a Chiralcel OD-H chiral column (eluted with isocratic 10:90 IPA/hexane, with 1.0 mL/minute flow rate; monitoring at 254 nm).

Example 10

Representative phenylzinc addition reaction catalyzed by (1S,2R,4R)-1,2-bis((7,7-dimethyl-2-morpholinobicyclo[2.2.1]heptan-1-yl)methyl)disulfane (IIIa)

To a toluene (4.0 mL) solution of phenylboronic acid (0.24 g, 2 mmol) was added diethylzinc (6.0 mL, 6 mmol 1.0 M in hexanes). The mixture was heated at 60° C. overnight and was then cooled to ambient temperature. The mixed zinc solution was transferred to another flask containing (1S,2R,4R)-1,2-bis((7,7-dimethyl-2-morpholinobicyclo[2.2.1]heptan-1-yl)methyl)disulfane (IIIa) (51 mg, 0.1 mmol) via syringe. After 10 minutes at ambient temperature, the mixture was cooled to 0° C. and neat p-tolualdehyde (108 μL, 1 mmol) was added dropwise. The reaction was stirred at 0° C. for 24 hours and was quenched by slow addition of sat. aq. $NH_4Cl$ (3 mL) and subsequent dilution with DCM (25 mL) and 1 N aq. HCl (30 mL). After layer separation, the aqueous solution was washed twice with DCM (20 mL). The DCM layers were combined, dried over $Na_2SO_4$, and concentrated to give a yellow oil which was purified by silica gel column chromatography (1:6 ethyl acetate:n-heptane) to give (R)-phenyl-p-tolyl-methanol as a white solid (0.147 g; 74% yield; 95.9% e.e.). The optical purity was determined by normal phase HPLC using a Chiralcel OD-H chiral column (eluted with isocratic 10:90 IPA/hexane, with 0.5 mL/minute flow rate; monitoring at 254 nm).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A process for preparing a compound of formula (I)

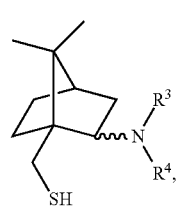

(I)

the process comprising:
i) contacting a sulfonamide of formula (II)

(II)

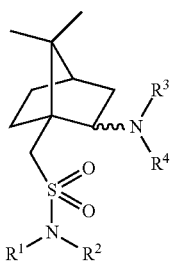

with a first reducing agent under conditions sufficient to provide a disulfide compound of formula (III)

(III)

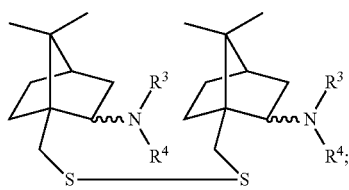

and
ii) contacting the disulfide compound of formula (III) with a second reducing agent under conditions suitable to form a compound of formula (I); wherein
$R^1$ and $R^2$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl;
$R^3$ and $R^4$ are independently H, benzyl, substituted benzyl, $C_{1-12}$ alkyl, $C_{3-10}$ cycloalkyl, $C_{4-9}$ heterocycloalkyl, $C_{6-10}$ aryl, or $C_{5-9}$ heteroaryl; or optionally
$R^3$, $R^4$, and N can together form a $C_{3-10}$ heterocycle.

2. A process according to claim 1, wherein the first reducing agent is an aluminum hydride reagent.

3. A process according to claim 2, wherein the aluminum hydride reagent is sodium bis(2-methoxyethoxy)aluminum hydride.

4. A process according to claim 1, wherein the second reducing agent is selected from the group consisting of a metal including zerovalent metals, zerovalent metal alloys, and non-zerovalent metals, a metal hydride and a highly reactive thiol.

5. A process according to claim 1, wherein $R^3$, $R^4$, and N together form a morpholine group.

6. A process according to claim 1, wherein the sulfonamide of formula (II) is the exo-diastereomer $II_x$ ($II_x$)

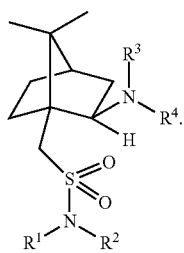

7. A process according to claim 1, the process further comprising:

iii) converting the compound of formula (I) to its acid salt (Is)

(Is)

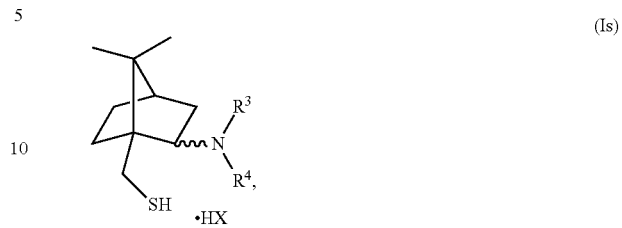

by contacting the compound of formula (I) with an acid (HX); wherein
HX is selected from the group consisting of an inorganic/mineral acid, a carboxylic acid, and an organic sulfonic acid.

8. A process according to claim 7, wherein the compound of formula (Is) is the exo-diastereomer.

9. A process according to claim 7, wherein the acid is HCl.

10. A process according to any of claims 1-6, wherein:
the compound of formula (I) is selected from the group consisting of compound (Ia) and the enantiomer of compound (Ia)

(Ia)

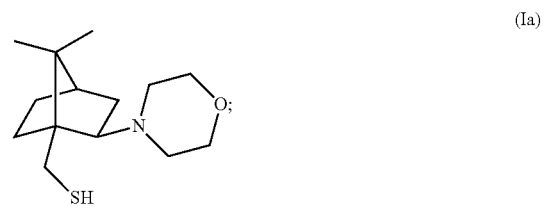 [SMILES: CC1(C)C2CCC1(CS)C(N1CCOCC1)C2]

the sulfonamide of formula (II) is selected from the group consisting of compound (IIa) and the enantiomer of compound (IIa)

(IIa)

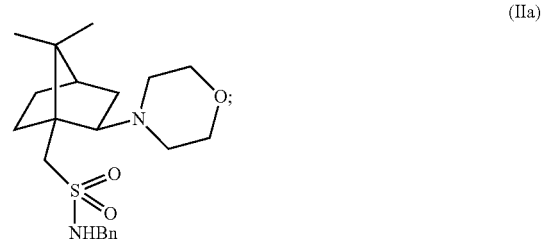

and
the compound of formula (III) is selected from the group consisting of compound (IIIa) and the enantiomer of compound (IIIa)

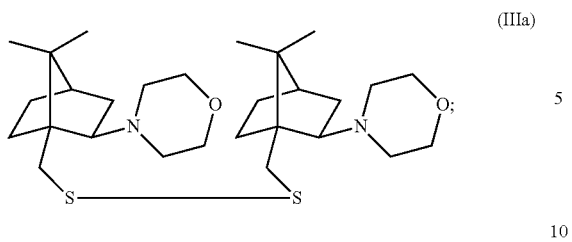
(IIIa)
with the proviso that if any one of the compounds of formula (I), (II), or (III) is present as a given enantiomer, then the other compounds have the same stereochemical configuration.
11. A process according to any of claims 7-9, wherein the compound of formula (Is) is selected from the group consisting of (Ib) and the enantiomer of compound (Ib)
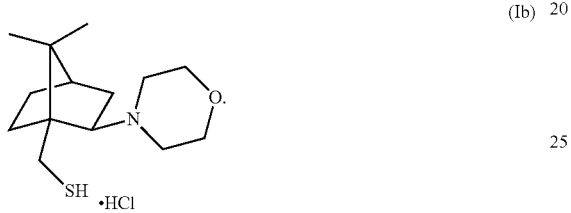
(Ib)
* * * * *